United States Patent [19]

Bri kus

[11] Patent Number: 4,902,479
[45] Date of Patent: Feb. 20, 1990

[54] CENTRIFUGAL ANALYZER ROTOR

[75] Inventor: Romas A. Bri kus, Brookline, Mass.

[73] Assignee: Fisher Scientific Company

[21] Appl. No.: 549,593

[22] Filed: Nov. 7, 1983

[51] Int. Cl.$^4$ ............................................. G01N 21/90
[52] U.S. Cl. ..................................... 422/72; 356/246;
356/427; 422/102
[58] Field of Search .................. 422/64, 102, 72, 104;
356/246, 427; 494/16, 38, 41

[56] References Cited

U.S. PATENT DOCUMENTS

4,225,558  9/1980  Peterson et al. ..................... 422/72
4,456,581  6/1984  Edelmann et al. ................... 422/104

FOREIGN PATENT DOCUMENTS

73512  3/1983  European Pat. Off. ............. 422/72

*Primary Examiner*—Michael S. Marcus
*Attorney, Agent, or Firm*—Fish & Richardson

[57] ABSTRACT

A multicuvette rotor for use in a centrifugal analyzer defines a circumferential array of elongated radially extending cuvettes and includes a one-piece body member of molded transparent material that has a planar upper surface and that defines a circumferential array of elongated cuvette recesses, and a one-piece cover member of molded transparent material that has a planar lower surface parallel to the planar upper surface of the body member with a continuous seal extending around each cuvette recess between the planar upper and lower surfaces to define the circumferential array of analytical cuvettes. Each elongated cuvette defines a first chamber for receiving a first constituent, a second chamber region for receiving a second constituent, divider structure between the first and second chamber regions over which the first constituent may be flowed into the second chamber region for forming a reaction product with the second constituent, and structure defining an analysis region adjacent the radially outer wall of the cuvette where the resulting reaction product is subjected to analysis. Barrier structure integral with the cover member extends along the surface of the cover member from the seal and inhibits premature mixing of the constituents due to wicking movement along the cover member of a constituent stored in one of the chamber regions to the other chamber region.

16 Claims, 1 Drawing Sheet

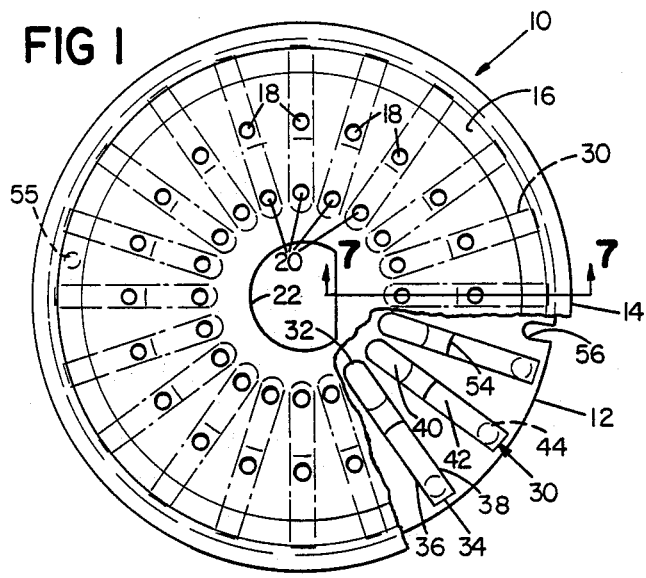
FIG 1
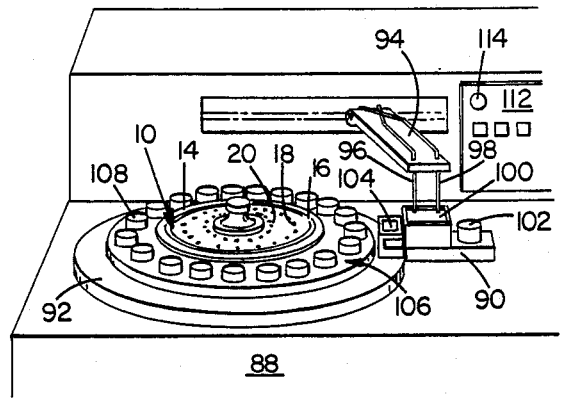
FIG 9
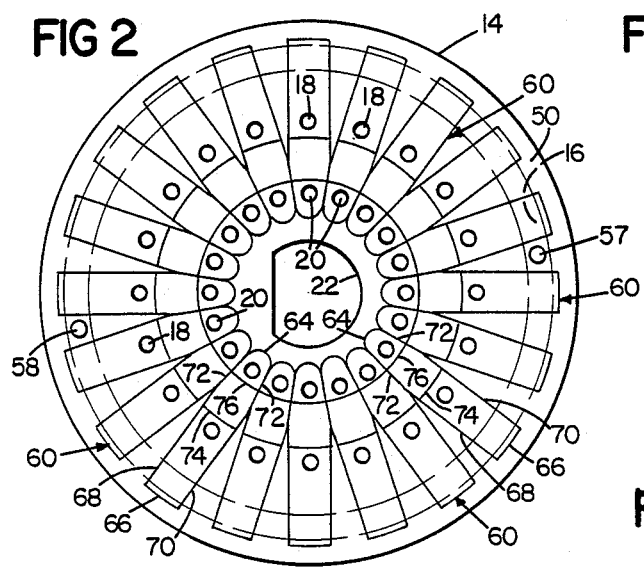
FIG 2
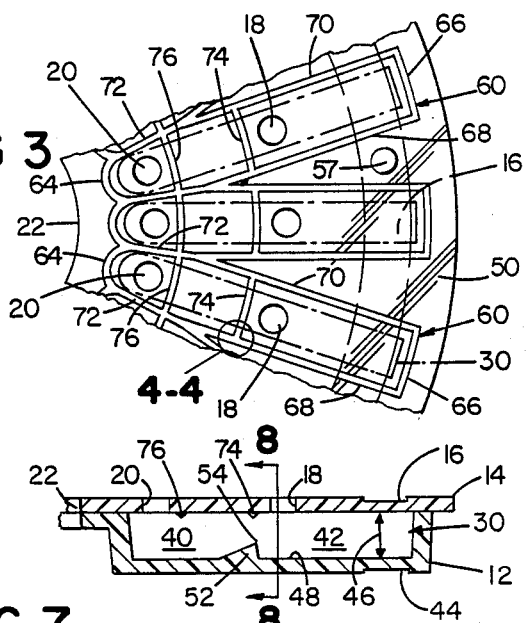
FIG 3
FIG 7
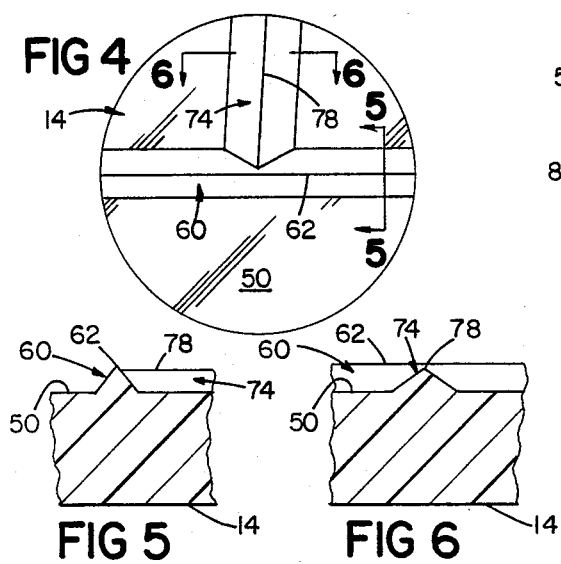
FIG 4
FIG 5   FIG 6
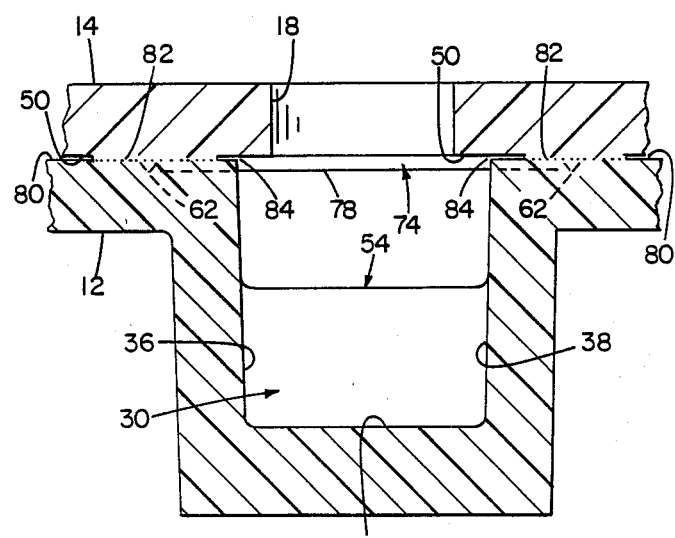
FIG 8

CENTRIFUGAL ANALYZER ROTOR

This invention relates to analytical systems, and more particularly to centrifugal analyzer cuvette rotors for use in centrifugal analyzer systems.

Centrifugal chemical analysis systems employ a rotor that has a circumferential array of spaced elongated radially extending cuvettes, each of which has two chambers for initially storing reagent materials separately and then transferring reagent material from one compartment to another for mixing and reaction, and subsequent analysis of the reaction in the analysis region by the cooperating instrument. Cuvette rotor assemblies of this type are disclosed in Tiffany et al. U.S. Pat. No. 4,226,531 and Stein et al. U.S. Pat. No. 4,373,812. In use of such rotors, sample to be analyzed (frequently with supplemental reagent material) is introduced through a loading port into one chamber and a second reagent material is introduced through a second loading port into the second chamber. The rotor disclosed in the above mentioned patent has twenty cuvettes that are loaded successively with automated loading equipment, small quantities of sample (2–20 microliters) being pipetted through loading ports into first chambers, and reagents in quantities up to 200 microliters being pipetted through loading ports into second chambers. The loaded cuvette rotor is then transferred to an analyzer for photometric, light scatter and/or fluorescence analysis. At the start of analysis, the rotor assembly is first spun at 100 rpm, then accelerated to about 4000 rpm in about one second for mixing sample and reagent, then braked to a full stop, and then brought to about 1000 rpm for analysis.

Numerous analytical tests are performed with such analyzers including, for example, glucose, creatinine, CPK, SGOT, triglyceride, and enzyme immunoassays. It has been found that there is an unacceptable tendency for reagent material to spontaneously move or "wick" along the upper surface of the cuvette resulting in premature mixing of reagents between the two chamber compartments, such mixing occurring in the case of some tests in less than one minute after loading, while the loading and incubation sequence may take fifteen minutes or more. For example, a drop of sample or reagent material (of several microliters in size) may adhere to the edge of a loading port and transfer from there along the surface of the cover. This problem is particularly significant with reagent materials that have high wettability characteristics such as reagents used in enzyme immunoassays, for example.

In accordance with one aspect of the invention, there is provided a multicuvette rotor for use in a centrifugal analyzer that defines a circumferential array of elongated radially extending cuvettes The rotor includes a one-piece body member of transparent material that has a planar upper surface and that defines a circumferential array of elongated cuvette recesses, and a one-piece cover member of transparent material that has a planar lower surface parallel to the planar upper surface of the body member with a continuous seal extending around each cuvette recess between the planar upper and lower surfaces to define the circumferential array of analytical cuvettes. Each elongated cuvette defines a first chamber for receiving a first constituent and a loading port in the cover member through which the first constituent is introduced into the first chamber region, a second chamber region for receiving a second constituent and a loading port in the cover member through which the second constituent is introduced into the second chamber region, divider structure between the first and second chamber regions that has a crest portion spaced from the lower surface of the cover member so that a transfer passage between the first and second chamber regions is defined through which the first constituent may be flowed into the second chamber region for forming a reaction product with the second constituent, and structure defining an analysis region adjacent the radially outer wall of the cuvette where the resulting reaction product is subjected to analysis. Barrier structure is located between the loading ports of the first and second chamber regions and extends from the seal at least to the upper edge of the cuvette sidewall adjacent the junction between the cover and body members for inhibiting premature mixing of the constituents due to wicking movement of a constituent stored in one of the chamber regions to the other chamber region along that junction.

In preferred embodiments, the seal is formed of melted energy director ridge material that extends about the periphery of each cuvette, and the barrier structure includes melted plastic material that merges with the melted energy director ridge material and obstructs a channel of capillary dimension that extends along the upper edge of a sidewall of a cuvette adjacent the junction between the cover and body members. While the energy director ridge and barrier structures may be formed on either the body member or the cover member, in a particular embodiment, the barrier structure is integral with the cover member. In preferred embodiments, the barrier structure also includes a ridge portion that extends transversely into the cuvette at least part way towards the opposed side wall from the melted plastic barrier structure material, and in particular embodiments the ridge portion extends uninterruptedly across the full width of the cuvette between its opposed sidewalls.

In a particular embodiment, the rotor assembly has a diameter of about ten centimeters and an overall height of about three-quarter centimeter, the cover member is a flat circular disc that has an optical window region, an outer circumferential array of loading ports, an inner circumferential array of loading ports, a substantially "D" shaped central opening, and opposed alignment posts that depend from its lower surface; and the body member has a flange in which are formed two alignment openings (one of which is radially elongated and outwardly open) in which the alignment posts are disposed, and a circumferential array of twenty individual cuvettes. Each cuvette of that rotor has a width of about ½ centimeter, and a length of about four centimeters, and has an analytical region defined by a pair of opposed optical windows adjacent the outer periphery of the rotor disc. That rotor embodiment includes a second barrier ridge portion in each cuvette, each barrier ridge portion extends transversely between the opposite sidewalls of the cuvette, each barrier ridge portion is spaced between one-half millimeter and five millimeters from the immediately adjacent loading port and one of the barrier ridge portions is in substantial alignment with the crest portion of the divider structure.

In centrifugal analyzer rotors in accordance with the invention, spontaneous mixing of sample and reagent due to wicking along the junction between cover and cuvette side walls is significantly impeded without increase in the size of the rotor or decrease in the number of the cuvettes.

Other features and advantages of the invention will be seen as the following description of a particular embodiment progresses, in conjunction with the drawing, in which:

FIG. 1 is a top plan view (with portions broken away) of a multi-cuvette rotor assembly in accordance with the invention;

FIG. 2 is a plan view showing the bottom face of the cover member of the rotor assembly shown in FIG. 1;

FIG. 3 is an enlarged view of a portion of that cover member;

FIG. 4 is a still further enlarged view of the portion of the cover member indicated at 4—4 in FIG. 3;

FIG. 5 is a sectional view taken along the line 5—5 of FIG. 4;

FIG. 6 is a sectional view taken along the line 6—6 of FIG. 4;

FIG. 7 is a sectional view taken along the line 7—7 of FIG. 1;

FIG. 8 is an enlarged sectional view taken along the line 8—8 of FIG. 7; and

FIG. 9 is a view of a loader mechanism for use with the rotor of FIG. 1.

DESCRIPTION OF PARTICULAR EMBODIMENT

The rotor assembly 10 shown in FIG. 1 has a diameter of about ten centimeters and an overall height of about three-quarter centimeter and is formed of an injection molded acrylic body member 12 and an injection molded acrylic cover member 14 that has the desired transparency, chemical resistance, and optical characteristics for photometric analysis. The cover member 14 is a flat circular disc that has an optical window channel 16, an outer circumferential array of loading ports 18, an inner circumferential array of loading ports 20, and a substantially "D" shaped central opening 22. Body member 12 has a circumferential array of twenty individual cuvettes 30, each of which has a length of about four centimeters between a cylindrical inner wall 32 and a planar outer wall 34; and a width of about 0.45 centimeter between parallel planar side walls 36, 38. Each cuvette has an inner chamber 40 which is loaded through port 20 and an outer chamber 42 which is loaded through port 18. Formed in the base of chamber 42 is a recessed optical window 44 aligned with optical channel 16 to provide an analysis region 46 that has an optical path length of one-half centimeter between cuvette base surface 48 and the parallel inner surface 50 of cover 14. In each cuvette 30 is divider ramp structure 52 that has a radial length of about six millimeters, a crest 54 that has a height of about ¼ centimeter, a planar inclined ramp surface that forms the rear wall of cuvette chamber 40 and a planar vertical surface that forms the inner wall of cuvette chamber 42, with chamber 42 having a static capacity of about 250 microliters. Formed in the flange web at the periphery of member 12 is circular opening 55 and diametrically opposed opening 56 in the form of a radially elongated slot that is open at the outer edge of the flange. Hole 55 and slot 56 each have a width of about three millimeters.

Further details of cover member 14 may be seen with reference to FIGS. 2-6. Member 14 is a disc that has a diameter of about ten centimeters and a thickness of about 1¼ millimeters. Disc 14 has planar lower surface 50 on which is formed an array of perimeter energy director ridges 60, each of which extends about the perimeter of an individual cuvette 30, as indicated in FIG. 3. Each perimeter ridge 60 is of triangular cross-sectional configuration with peak 62, as indicated in the view of FIG. 5 and has a height of about 0.3 millimeter and a base width of about 0.5 millimeter; and includes arcuate inner wall section 64, outer wall section 66, parallel sidewall sections 68, 70, spaced apart about 0.7 centimeters and shared sidewall sections 72. Also projecting from surface 50 are two slightly tapered (2°) alignment posts 57, 58, each of which has a length of about 1½ millimeters and a base diameter that is about 0.05 millimeter less than the width of openings 55, 56.

A first set of barrier ridges 74 extends between the energy director sidewall ridges 68, 70 at a radius of about three centimeters, ridge 74 being located about ¼ centimeter radially inwardly from loading port 18. A second set of barrier ridges 76 (essentially in the form of a ring that merges with the common wall portions 72 of perimeter ridge 60) is located at a radius of about 2.1 millimeters (spaced about one millimeter radially outwardly from loading port 20). Each barrier ridge 74, 76 is of triangular cross-sectional configuration (as indicated in FIG. 6) and has a base width of about 0.8 millimeter, a height of about ¼ millimeter such that its peak 78 is slightly lower than the peak 62 of energy director ridge 60 and a peak 78. Barrier ridges 74 and 76 merge with sidewall ridges 68 (70, 72) as indicated in FIG. 4.

In sealing cover 14 to body 12, cover 14 is placed on the upper surface of body 12 with cover alignment posts 57, 58 disposed in body flange openings 55, 56 and with the crests 62 of the peripheral ridges 60 resting on surface 80 such that cover surface 50 is spaced about 0.3 millimeter from body surface 80 (FIG. 8). Slot 56 allows post 58 to move radially so that crests 62 may be firmly seated on surface 80 with accurate alignment of ridges 60 with their cuvettes 30. Cover 14 is then ultrasonically welded to body 12 with a horn pressure of about 60 psi and application of twenty kilohertz energy for about one second. That ultrasonic energy melts the energy director ridges 60 and creates a peripheral seal (as indicated at 82 in FIG. 8) about each cuvette 30. The melted plastic material flows along surfaces 50 and 80 but frequently a small gap 84 (typically less than 0.1 millmeter in width) remains between cover surface 50 and body surface 80 adjacent cuvette side wall 36, 38. This gap 84 has been found to induce rapid capillary "wicking" action that transfers any reagent that contacts it from one compartment 40 or 42 to the other compartment with resultant premature mixing. The barrier ridges 74, 76 are also melted during the ultrasonic welding in those regions where they overlie body surface 80 producing a weld type merger of plastic material that fills and obstructs each crevice area 84 with each barrier ridges 74, 76 of each cuvette 30 extending from each merger area across the entire width of the cuvette between the cuvette sidewalls 36, 38.

Thus, while a droplet of reagent material which adheres to the edge of loading port 18 (or loading port 20) may rapidly wick by capillary action along crevice channel 84, each such channel is filled and blocked by the melted merged portions of barrier ridges 74. These barrier structures thus inhibit spontaneous premixing of reagent materials by flow either along the cover surface 50 or along a channel 84 from one chamber 40, 42 to the other.

With reference to FIG. 9, a micropipetter-loader system 88 has a reagent supply module 90, an indexed platform 92 that receives rotor 10 and a transport arm 94 that carries two pipette tubes 96, 98. Module 90 includes a washbath 100, a first reagent supply 102 and a second reagent supply 104. A sample ring 106 positions twenty sample cups 108 concentrically around rotor 10 in alignment with cuvettes 30. Samples, standards, and controls are placed in the sample cups 108 and reagents are poured into the reagent supply containers 102, 104. Pipetter-loading control selections are made by setting mode switches on control panel 112. In response to depression of start switch 114, transport arm 94 moves to washbath 100 where the tips of pipette tubes 96, 98 are submerged and washed by raising platform 92. The platform then lowers and transport arm 94 travels to a position where sample tube 96 is directly over a sample cup 108 and reagent tube 98 is over reagent boat 104; the platform lifts and the pipette tips are submerged into the sample and reagent vessels, and preselected volumes of sample and reagent are drawn into the pipettes. Platform 92 then lowers and the arm 104 moves to reagent and sample ports 18, 20 in rotor 10. Again platform 92 is raised so that the tips of pipette tubes 96, 98 enter ports 18, 20 and the aspirated sample and reagent volumes are dispensed into chambers 40 and 42 of the aligned cuvette 30. During this dispensing operation, a droplet of dispensed reagent may adhere to the edge of a loading port and be located sufficiently close to gap 84 to be attracted by capilliary action for flow to and along that gap. This flow is blocked by the melted portions of barrier ridges 74 that fill those gaps. The platform 92 then lowers and the rotor 10 is indexed to the next cuvette position for loading sample and reagent volumes into the next cuvette in a similar cycle. Each cuvette loading cycle is about thirty seconds in duration.

In this embodiment, a selected sample volume in the range of 2-20 microliters (optionally with a volume of supplemental reagent material) is dispensed in the chamber 40 and a selected reagent volume in the range 150-200 microliters is dispensed into chamber 42 depending on the particular test involved. As indicated above, as the sample and reagent volumes flow into their respective cuvettes, a drop of the dispensed liquid may adhere to the edge of the loading port, and the adjacent gap or channel 84 between cover 14 and body 12 may draw that drop of liquid in capillary wicking action. That wicking action, however, is inhibited by the barrier structure 74, 76 such that spontaneous mixing of reagents due to such capillary wicking action between the two chambers of the cuvette is effectively prevented.

After the twenty cuvettes 30 of rotor 10 have been loaded, the rotor is transferred to an analyzer for incubation, centrifugal acceleration to provide transfer of the sample (and reagent) from chamber 40 to analysis chamber 42 and mixing. The rotor is then braked and then accelerated again to about 1000 rpm for photometric analysis. The capillary flow barrier structures of ridges 74, 76 retard spontaneous "wicking" and 'creep' type flows of reagent in either direction from one chamber to the other while not interfering with transfer of sample and reagent from chamber 40 to chamber 42 under centrifugal force nor with the mixing and analysis steps.

While a particular embodiment of the invention has been shown and described, various modifications will be apparent to those skilled in the art, for example, energy director ridges 60 and barrier ridges 74 may be formed on the upper surface of body 12 rather than on the lower surface of cover 14; and therefore it is not intended that the invention be limited to the disclosed embodiment or to details thereof and departures may be made therefrom within the spirit and scope of the invention.

What is claimed is:

1. A multicuvette rotor for use in a centrifugal analyzer, said rotor defining a circumferential array of elongated radially extending cuvettes and comprising a one-piece body member of transparent material that has a planar upper surface and that defines a circumferential array of elongated cuvette recesses, and a one-piece cover member of transparent material that has a planar lower surface parallel to said planar upper surface of said body member, seal means including continuous seal structure extending around each said cuvette recess between said planar upper and lower surfaces to define said circumferential array of analytical cuvettes, each said elongated cuvette including structure defining a first chamber for receiving a first constituent and a loading port in said cover member through which said first constituent may be introduced into said first chamber region, structure defining a second chamber region for receiving a second constituent and a loading port in said cover member through which said second constituent may be introduced into said second chamber region, structure defining a radially outer wall, and structure adjacent said radially outer wall defining an analysis region, said seal means further including barrier structure in each cuvette, each said barrier being connected to said lower surface of said cover and located between the loading ports of said first and second chamber regions and extending from said seal structure at least to the upper edge of a sidewall of said cuvette adjacent the junction between said cover and body members for inhibiting wicking movement along said cove member of a constituent stored in one of said chamber regions to the other chamber region and premature mixing of said constituents, and divider structure between said first and second chamber regions in each cuvette, each said divider structure being connected to the upper surface of a bottom wall of said cuvette recess and having a crest portion spaced from said lower surface of said cover member so that a transfer passage between said first and second chamber regions is defined between said crest portion and said lower surface of said cover member through which said first constituent may be flowed into said second chamber regions for forming a reaction product with said second constituent.

2. The rotor of claim 1 wherein said barrier structure obstructs a channel of capillary dimension that extends along the upper edge of a sidewall of a said cuvette adjacent the junction between said cover and body members.

3. The rotor of claim 1 wherein said barrier structure is integral with said cover member and includes a ridge portion that is less than one millimeter in height and that extends transversely from said seal structure towards an opposed sidewall of a chamber region.

4. The rotor of claim 3 wherein said ridge portion extends uninterruptedly between the opposed sidewalls of a chamber region.

5. The rotor of claim 1 wherein said seal structure includes melted energy director ridge material that extends about the periphery of each said cuvette.

6. The rotor of claim 5 wherein said barrier structure is composed of plastic material that merges with said energy director ridge material 7. The rotor of claim 6 wherein said cover member is a flat circular disc that has an optical window region adjacent its outer periphery, an outer circumferential array of loading ports, an inner circumferential array of loading ports, a substantially "D" shaped central opening, and a plurality of alignment posts depending from its lower surface; and said body member has a flange in which are disposed a plurality of alignment openings in which said alignment posts are received, at least one of said alignment openings being radially elongated and outwardly open.

8. The rotor of claim 1 wherein said barrier structure is integral with said cover member and includes a first ridge portion that is less than one millimeter in height and that has a sharp crest.

9. The rotor of claim 8 wherein each said cuvette includes spaced opposed sidewalls, and further including a second barrier ridge portion in each said cuvette, each said barrier ridge portion extending transversely between said sidewalls of said cuvette.

10. The rotor of claim 9 wherein each said barrier ridge portion is spaced at least one-half millimeter from the loading port adjacent said barrier ridge portion.

11. The rotor of claim 9 wherein each said barrier ridge portion is spaced less than five millimeters from the loading port adjacent said barrier ridge portion.

12. The rotor of claim 8 wherein each said barrier ridge portion is in substantial alignment with the crest portion of said divider structure.

13. The rotor of claim 1 wherein said seal structure includes energy director ridge material that extends about the periphery of each said cuvette, and said barrier structure includes a ridge portion that extends transversely of each said elongated cuvette along said planar lower surface of said cover member between the spaced sidewalls of a chamber region of each said cuvette and plastic material at either end of said ridge portion that merges with said energy director ridge material.

14. The rotor of claim 13 wherein said plastic material at said end of said ridge portion obstructs a channel of capillary dimension that extends along the upper edge of a sidewall of a said cuvette adjacent the junction between said cover and body members.

15. The rotor of claim 13 and further including a second barrier ridge portion in each said cuvette that extends transversely of each said elongated cuvette along said planar lower surface of said cover member between the opposite sidewalls of said cuvette, each said barrier ridge portion being spaced at least one-half millimeter and less than five millimeters from the adjacent loading port, and wherein one of said barrier ridge portions in each said cuvette is in substantial alignment with the crest portion of said divider structure in that cuvette.

16. The rotor of claim 15 wherein said plastic material at each end of each said ridge portion obstructs a channel of capillary dimension that extends along the upper edge of a sidewall of a said cuvette adjacent the junction between said cover and body members.

* * * * *

UNITED STATES PATENT AND TRADEMARK OFFICE
CERTIFICATE OF CORRECTION

PATENT NO. : 4,902,479
DATED : February 20, 1990
INVENTOR(S) : Romas A. Brickus

It is certified that error appears in the above-identified patent and that said Letters Patent is hereby corrected as shown below:

In the "[75] Inventor" section, "Bri kus" should be --Brickus-- and [19]

In the "[65] References Cited" section, add the following references:

| Document No. | Date | Name |
|---|---|---|
| 3,586,484 | 06/22/71 | Anderson |
| 3,759,666 | 09/18/73 | Hill |
| 3,798,459 | 03/19/74 | Anderson |
| 3,813,031 | 05/28/74 | Anderson |
| 3,873,217 | 03/25/75 | Anderson |
| 3,899,296 | 08/12/75 | Mailen |
| 4,123,173 | 10/31/78 | Bullock |
| 4,226,531 | 10/07/80 | Tiffany |
| 4,373,812 | 02/15/83 | Stein |

Col. 4, line 44, "millmeter" should be --milllmeter--.

Col. 7, line 9, after "material", insert a period.

Signed and Sealed this

Twenty-second Day of October, 1991

Attest:

HARRY F. MANBECK, JR.

Attesting Officer

Commissioner of Patents and Trademarks